| United States Patent [19] | [11] Patent Number: 4,831,024 |
| Vreman et al. | [45] Date of Patent: May 16, 1989 |

[54] METHOD TO PREVENT NEONATAL JAUNDICE

[75] Inventors: Hendrik J. Vreman, Los Altos; David K. Stevenson, Palo Alto, both of Calif.

[73] Assignee: The Board of Trustees of the Leland Stanford Junior University, Stanford, Calif.

[21] Appl. No.: 108,743

[22] Filed: Oct. 15, 1987

[51] Int. Cl.$^4$ .................... A61K 31/555; A61K 49/00
[52] U.S. Cl. .......................................... 514/185; 424/9
[58] Field of Search .................... 424/9; 514/185, 184

[56] References Cited

PUBLICATIONS

Qato et al., "Prevention of Neonatal Hyperbilirubinaemia in Non-Human Primates by Zn-protoporphyrin" Biochem J 226(1), 51-7(1985).

*Primary Examiner*—Stanley J. Friedman
*Assistant Examiner*—Richard Kearse
*Attorney, Agent, or Firm*—Irell & Manella

[57] ABSTRACT

Disclosed herein is an effective and safe method for preventing the onset of neonatal jaundice through the reduction of bilirubin production. This method can be applied to populations of infants based on mass screening procedures predictive of development of the disease. The most effective of these screening methods measures carbon monoxide production by the infants using a simple breath test.

11 Claims, 1 Drawing Sheet ns (Ostrander, C. R. et al. *J Lab Clin Med* (1982) 100: 745-755).

METHOD TO PREVENT NEONATAL JAUNDICE

REFERENCE TO A GOVERNMENT GRANT

The Government has rights in this invention pursuant to NIH Grant HD14426, awarded by the Department of Health and Human Services.

TECHNICAL FIELD

The invention relates to the field of clinical medicine and epidemiology. More specifically, the invention concerns a method to screen human subjects for incipient hyperbilirubinemia and to prevent jaundice in subjects at risk.

BACKGROUND ART

Infant jaundice, or hyperbilirubinemia, is a significant clinical problem, occuring in about 5% of full-term infants. The syndrome is the direct result of increased bilirubin levels in the infant body. Adults also have problems with jaundice, but they are generally not as serious or as widespread because most adults are capable of conjugating excess bilirubin with sugars and clearing this toxin from the body. This detoxification mechanism is not fully developed in neonates. Nevertheless, some adults, such as those who have hepatitis or obstructions to bile flow, are subject to jaundice as well.

Various treatments have been suggested for both infant and adult jaundice when these problems occur. These treatments include phototherapy, exchange transfusions, extracorporeal filtration systems, and drugs which induce an efficient clearance system. None of these treatments is simple to administer or effective without negative side reactions, including risk of injury or death. If the jaundice is not promptly treated, serious damage to the nervous system can result, especially in infants, as the elevated amounts of bilirubin act as a neurotoxin, and the blood/brain barrier in infants is incompletely developed. Also, the foregoing treatments are administered after the fact—i.e., after the jaundice has already appeared.

In neonates, the visible signs of the disorder manifest themselves usually at about 72 hours after birth, often after the infant has left the hospital or birth center. Thus, the signs may appear when the baby is no longer under the observation of trained medical personnel. In order to minimize the organic and neurological damage caused by the elevated bilirubin levels, therefore, it is advantageous to intervene before control over treatment has been lost, which is often before the signs actually appear.

One aspect of effective intervention is the identification of individuals at risk for developing this syndrome. Because, in order to eliminate as totally as possible the incidence of neonatal jaundice, every infant must be tested, effective prediction requires a simple, noninvasive procedure. Measurement of bilirubin in the blood per se is not a satisfactory approach because accurate prediction of a potential to develop jaundice rests on detection of increased bilirubin production, as opposed to the levels of bilirubin in the blood. Blood bilirubin levels are influenced not only by production, of course, but also by rates of excretion, and hepatic and intestinal uptake.

Excreted CO rate serves as a valid measure of bilirubin production because CO is a byproduct of the oxidation of heme by heme oxygenase and this is the major source of carbon monoxide generated from metabolic processes (Ostrander, C. R. et al. *J Lab Clin Med* (1982) 100: 745-755).

It has been shown that a simple noninvasive test for CO production can be used to predict, the risk for development of hyperbilirubinemia in infants, and, more importantly, also identify infants who will not have serious jaundice with high accuracy. Smith, D. W. et al. *Pediatrics* (1985) 75: 278-280, shows a high correlation between positive results in measurement of carbon monoxide concentration in a mixed end-expiratory gas collection—i.e., an "end-tidal sample" ($ET_{CO}$) and subsequent development of jaundice. The breath carbon monoxide concentration directly correlates with bilirubin production as measured by the CO excretion rate. This correlation has been shown by, for example, Smith, D. W. et al. *J Pediatric Gastroenterology and Nutrition* (1984) 3: 77-80. This latter paper showed that $ET_{CO}$ is directly related to the pulmonary excretion rate of CO, which is known to be a measure of bilirubin production, but which must be measured using a complex breathing apparatus which encases the infant's head. $ET_{CO}$, on the other hand, permits the expired gas to be drawn through a simple nasal catheter. Improvements have also been made in the technique for measuring the CO per se, as disclosed in its application to CO measurement in sample tissues, such as blood (Vreman, H. J., et al, *Clin Chem* (1987) 33: 694-697.

Not only does $ET_{CO}$ correlate well with bilirubin production, its predictive value in identifying subjects not at risk to develop jaundice is virtually completely successful—i.e., those who show normal $ET_{CO}$ values are virtually certain not to develop a metabolically serious form of this syndrome. About 60% of those with elevated levels go on, if not treated, to show the signs of jaundice. Because $ET_{CO}$ is related to hemolysis, it identifies only those who will develop serious jaundice with dangerous medical effects on the patient.

When subjects at risk are identified, they must either be monitored for subsequent treatment or administered a treatment in advance which prevents the onset of serious jaundice. Because heme oxygenase is an essential enzyme for the production of bilirubin, inhibitors of this enzyme have been suggested as chemopreventive agents. The use of tin protoporphyrin has been suggested as such an agent by Drummond, G. S. and Kappas, A. *Science* (1982) 217: 1250-1252. However, tin, when administered at high levels in most forms is toxic, and administration of this compound carries sufficient inherent hazard that its use as a preventative is subject to considerable hesitation and reluctance. Even if only 40% of the neonates with elevated $ET_{CO}$ levels do not, in fact, need to be treated with a preventative, the possibility that the infant is being subjected to an unnecessary risk is clearly an inhibition to administering this agent. McDonagh, A., *J Photochem Photobiol* (1987) 1: 127-133 estimates that 1 mg/kg doses of tin protoporphyrin can be tolerated by humans; this may be an upper limit.

The zinc analog of the tin compound has also been suggested for chemoprevention (Qato, M. K. and Maines, M. D. *Biochem J* (1985) 226: 51-57, however, its efficacy is controversial as it appeared to be ineffective in the hands of Drummond and Kappas (supra). In fact, neither group demonstrated its effect, shown hereinbelow, on bilirubin production.

Drummond and Kappas (supra) found that zinc protoporphyrin at doses up to 50-fold greater than the effective dose of tin protoporphyrin did not prevent increase in tissue heme oxygenase activity and serum bilirubin levels. While the Qato paper suggests the use of zinc protoporphyrin for prevention of neonatal hyperbilirubinemia, Drummond showed that only at extremely high dosage levels (500 umol/kg) was zinc protoporphyrin able to lower, after a considerable, 7 day, lag period, hepatic heme oxygenase activity in rats, and was unable to prevent the normal postnatal rise in the levels of this enzyme, or the postnatal rise in plasma bilirubin. Tin protoporphyrin in their hands was effective at 10 umol/kg. Qato, however, found that zinc protoporphyrin administered at 40 umol/kg subcutaneously into nonhuman primates was able to lower serum bilirubin levels and to inhibit the activity of heme oxygenase in the liver and spleen. These results appear to conflict with those obtained by Drummond.

Zinc protoporphyrin, like zinc compounds generally, has the advantage of a virtual absence of toxicity as zinc is an essential element which is nearly as abundant as iron. It has an established minimum daily requirement of about 3 mg/day, or about 50 umol/day in neonates. At these levels, zinc complexes are completely safe, and could be used with little hesitation for preventive therapy; the 40% of infants in the high $ET_{CO}$ group who in fact are not in need of chemoprevention would not be harmed by its administration.

The present invention provides a synthesis of the potentially useful zinc protoporphyrin-related chemoprevention regime with a noninvasive screening procedure to provide a systematic program for prevention of neonatal jaundice. The approach can be applied, if desired, to adult jaundice as well.

DISCLOSURE OF THE INVENTION

The invention provides a program for the elimination of the problem of neonatal jaundice. A noninvasive, highly predictive screening procedure is used in combination with a safe and effective method for chemoprevention to permit this hazard of newborn existence to be eliminated. The noninvasive screen involves the use of a simple breath test. Subjects found to be at risk in this simple screening procedure are then administered an effective amount of zinc protoporphyrin or zinc protoporphyrin analog to prevent the onset of this syndrome. The use of the screen avoids the too-extensive administration of even these very safe drugs. The use of safe drugs permits the entire at-risk subpopulation to be protected without fear of unnecessary side effects.

Thus, in one aspect, the invention is directed to a method to prevent the occurrence of neonatal jaundice in a population of human infants which comprises, first, screening the members of the population for above-normal carbon monoxide production, and, second, administering to members of this population who exhibit above-normal carbon monoxide production, an amount of zinc protoporphyrin or derivative thereof effective to reduce the production of bilirubin. In another aspect, the invention is directed to pharmaceutical compositions effective in this method.

MODES OF CARRYING OUT THE INVENTION

Figure 1:
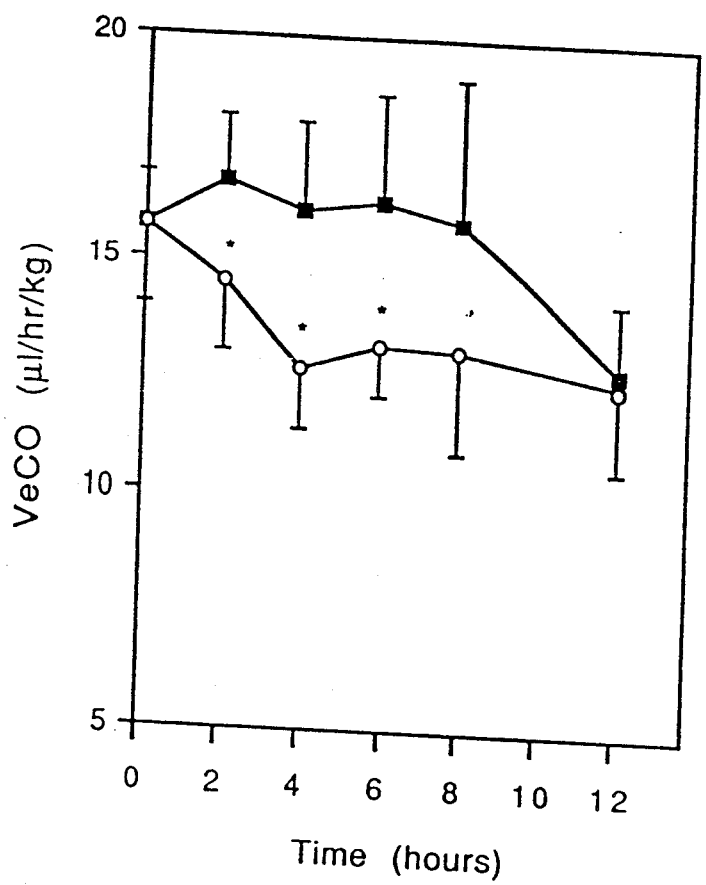
FIG. 1 shows the effect of zinc protoporphyrin administration on CO excretion of adult rats.

The population of neonates in birth centers is screened, according to the method of the invention, to determine that subpopulation with a high probability of becoming affected by jaundice caused by excess bilirubin production. The screen comprises a non-invasive test which is administered within a few hours after birth, preferably less than 12 hours after birth. An effective and noninvasive screen consists simply of a determination of $ET_{CO}$. If desired, of course, this can be supplemented with indicia of bilirubin levels (as opposed to production) such as the photometric measurement of skin color. The test for skin color can be administered using commercially available equipment; see, for example, the directions for this test published by Hannemann, R. E., et al, *Pediatrics* (1982) 69: 107–109. However, because $ET_{CO}$ measures the production of bilirubin, it reveals those subjects who will be seriously at risk due to the hemolysis associated with this production; high bilirubin levels as measured by transcutaneous color may be due to other, less life-threatening causes.

As described by Smith, D. W. et al. *J Pediatric Gastroenterology and Nutrition* (1985) 4: 38–44, incorporated herein by reference, samples of end-expiratory breath are collected by transnasal placement of a 5 French catheter (Pharmacyl Inc., Toa Alta, PR) into the posterior nasal pharynx. The expired gas is drawn in small, less than 1 ml, increments at end-expiration as determined by the infants chest wall movement. A syringe of sufficient size, for example 12 cc, and sealed by a 3-way stopcock is used to permit the collection of a total of approximately 10 mls of expired breath. Sample collection, therefore, takes less than a minute. However, if desired, duplicate or triplicate samples can be taken and that with the highest CO concentration chosen as most representative of alveolar gas. The samples measured should be corrected for the contribution of CO from room air ($RA_{CO}$) which can vary in the range of 0.2–3 ul/l. When corrected for the $RA_{CO}$, normal infants measured at 24 hours, show 1.44 ul/l±0.48 standard deviation. When measured soon after birth, the normal range is considered approximately 1–1.5±0.40. Infants having an $ET_{CO}$ measured at above about 2 ul/l are thus considered at risk. Some infants show levels as high as 5–8 ul/l. (Premature infants, which have, in fact, a higher risk for neonatal jaundice have a higher normal range of $ET_{CO}$, i.e., 1.64±0.53 ul/l.) The CO in the samples is measured most accurately using gas chromatography and the results are available within minutes.

In the method of the invention, subjects which show $ET_{CO}$ levels greater than 2 ul/l are considered to be at risk and are administered zinc protoporphyrin or a derivative thereof as a chemopreventive agent. Effective doses are typically in the range of 0.1–100 umol/kg, preferably <1 umol/kg. In a typical protocol, only a single treatment is given, however, administration of this dosage at 1 dosage per day for 4–5 days can also be used.

The zinc protoporphyrin is administered in a formulation suitable for injection subcutaneously, intramuscularly, intraperitoneally, or intravenously, preferably IV or IM. Oral administration may also be used. For such injectable formulations, the drug is prepared as a solution or suspension, or in a solid form suitable for reconstitution as a solution or suspension, or as an emulsion. Suitable excipients are, for example, water, saline, dextrose, glycerol, and so forth. The compositions to be administered may also contain minor amounts of nontoxic auxiliary substances such as wetting or emulsifying agents, pH buffering agents and the like such as, for example, sodium acetate, sorbitan monolaurate, and so forth.

By zinc protoporphyrin derivatives is meant complexes of zinc with various porphyrin-related materials, such as porphyrins containing alternate side-chains to those contained in protoporphyrin, as well as chlorins and phlorins. These classes differ from the porphyrins only by the degree of hydrogenation of the tetrapyrole nucleus. Thus, included within the scope of the invention are zinc compounds of the general formula

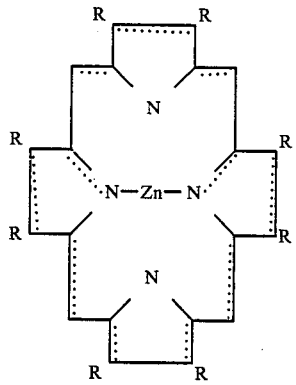

wherein
each R is independently selected from the group consisting of H and lower alkyl or alkenyl (1-6 C) optionally containing one or more functional groups; and
the dotted lines represent the presence or absence of a pi-bond at the indicated location.
(When a pi-bond is absent, at the C to which "R" is attached, there are, of course, two independently selected Rs present).

For example, in protoporphyrin-9, all of the dotted lines represent pi-bonds and the designated R groups are, reading clockwise from the top, methyl, vinyl, methyl, vinyl, methyl, 2-carboxyethyl, 2-carboxyethyl and methyl. In etioporphyrin, these substituents are, reading clockwise, methyl, ethyl, methyl, ethyl, methyl, ethyl, ethyl, methyl. These analogs are merely illustrative, and a variety of zinc-containing porphyrin derivatives are commercially available. A preferred embodiment of said tetrapyrrole analogs is zinc mesoporphyrin. A number of such analogs are available commercially, for example, from Porphyrin Products, Logan, Utah.

An improved method of evaluating the effects of various zinc protoporphyrin derivatives on heme oxygenase activity in whole animals and in tissue samples permits convenient testing for efficacy of various types of derivatives. See, for example, Hamori, C. J. et al. "Zinc Protoporphyrin Inhibits Bilirubin Production in Adult Rats" *J Pediatric Gastroenterology and Nutrition* (1987) (in press); Vreman, H. J. et al. "Direct Measurement of Heme Oxygenase Activity by Gas Chromatography" *Abstracts: American Pediatric Society and Society for Pediatric Research* (1987), Ser. No. 06194 and *Anal. Biochem* (in press). By assessing the ability of a particular zinc-containing porphyrin derivative to suppress heme oxygenase activity either in isolated tissues or in whole animals, its appropriateness as a chemopreventive in the method of the invention can be readily assessed.

Typically, in the application of the method of the invention, the method is practiced as a routine procedure for newborns. Each newborn is tested for $ET_{CO}$ within a few hours after birth, and the results obtained.

As the test is simple and straightforward, results will be available within minutes after administration of the test. The results are matched against the above referenced norms, and infants having an enhanced $ET_{CO}$ value of greater than 2 ul/l are treated with a standard 0.1-100 umol/kg dosage of zinc protoporphyrin or its derivative, usually by injection. A dosage of 1 umol/kg or less is preferred. In general, one administration of the drug will suffice. The infant can then be released although it may be advisable to retain follow-up procedures in cases where exceptionally high $ET_{CO}$ is found.

By use of the protocol and method of the invention the chemopreventive drug, however safe, is nevertheless not administered to the total infant population. It is generally recognized that exposure to drugs should be minimized in the general population, and only those subjects at risk should be thus exposed. By using the screening procedure in combination with the administration of the chemopreventive, it has been found that only approximately 10% of newborns will be judged to require administration of the drug. The screen has been shown to be successful in finding all subjects at risk, in only about 40% of these cases will the administration of the chemopreventive turn out, in retrospect, to have been unnecessary. Because of the safety of the drug, however, this can be considered harmless error.

EXAMPLES

The following examples are intended to illustrate but not to limit the invention.

EXAMPLE 1

Inhibition of Bilirubin Production in the Adult Rat by Zinc Protoporphyrin

Adult male and female Wistar rats (280-380 g) were housed at 25° C. with a 12 h light cycle and were fed on unlimited Wayne MRH 22/5 Rodent Blox (Continental Grain Co., Chicago, IL) and water. The animals were weighed and placed in air-tight plexiglass containers supplied with CO-free air at a known flow rate. After a 1 hr equilibration period, air leaving the chamber was analyzed for CO concentration by gas chromatography according to the method of Ostrander, C. R., et al, *Anal Biochem* (1982) 119: 378-386. Samples were taken every 15 min for at least 75 min. A baseline value for excretion of CO ($VE_{CO}$) was determined and at time 0, the rats were subcutaneously injected with either 40 micromol/kg of zinc protoporphyrin dissolved in 0.1M phosphate buffer, pH 7.4 or an equal volume of saline. $VE_{CO}$ measurements were taken at 2, 4, 6, 8, and 12 h.

The results are shown in FIG. 1. These results show suppression of $VE_{CO}$ over a 12 hr period. The solid squares show $VE_{CO}$ for the controls (n=8); the open circles shown $VE_{CO}$ for the rats administered the drug (n=8).

EXAMPLE 2

Metabolism of TP and ZP by Tissue Homogenation

Liver, spleen, kidneys and intestines were removed from decapitated fed adult female Wistar rats (250-300 g). The content of the intestine was removed by flushing the lumen with phosphate buffer. All tissues were homogenized in a biohomogenizer (Biospec Products, Inc., Bartlesville, OK) in four volumes of 0.1M potassium phosphate buffer, pH 7.4. The homogenate was centrifuged for 15 min at 13,000×g and the supernatant was utilized in the studies below.

Production of CO by these supernatants without the addition of any substrate (background) and in the presence of 400 uM heme, tin protoporphyrin (TP) or zinc protoporphyrin (ZP) was determined. The reactions were conducted with 1.8 mM NADPH (total) or without addition of NADPH (blank). The NADPH-supported CO production rate, which represents heme oxygenase activity is obtained by subtracting the blank rate from the total rate.

Heme oxygenase activity was tested by conducting the reaction in 2 ml vials sealed with screwcap and septum wherein the headspace had been purged with CO-free air for 2 sec at a flow rate of 200-300 ml/min. Ten ul of supernatant was incubated with 20 ul of substrate under the conditions described above at 37° C. for 15 min. The reactions were terminated by transfer of the vials to −78° C. (acetone/dry ice). The generated CO was determined by analyzing the entire head space volume by gas chromatography using a Reduction Gas Analyzer (Trace Analytical Inc., Menlo Park, CA) with a limit of detection of 1 pmole CO/vial. The analyzer was calibrated with a mixture of CO in nitrogen. Heme oxygenase activity was expressed as nmoles CO/hour/mg protein. A more detailed description of this method to determine the activity of heme oxygenase appears in Vreman, H. J. and Stevenson, D. K., *Anal Biochem* (1987) (in press).

The results showed that both heme and tin protoporphyrin were metabolized by heme oxygenase as judged by NADPH-dependent CO generation. Zinc protoporphyrin was, however, not a substrate for this enzyme, although non-NADPH dependent CO generation was detected in low amounts from ZP.

EXAMPLE 3

Formulation of ZP for Injection

For injection as a unit dose, 6.3 mg of zinc-protoporphyrin were dissolved in 500 ul 1N NaOH with mixture for 5 minutes. To this was added 2.5 ml 0.4M Na3PO4 and mixing was continued for 5 minutes. After addition of 2.5 ml distilled water, the pH was gradually adjusted to 7.4 with 1N HCl. The final volume was adjusted to 10 ml with distilled water. All procedures were carried out in subdued light. The resulting solution has a ZP concentration of 1 mM.

CONCLUDING REMARKS

The method of the invention offers a sound approach to the prevention of neonatal jaundice. As noted by McDonagh, A. F. *J Photochem Photobiol* (1987) (supra), the more toxic drug, tin protoporphyrin is being tested in newborns in Greece without the benefit of a screening procedure to identify those infants in need of chemoprevention. Exposure of the entire population of neonates to a potentially harmful drug is clearly not as conservative an approach as that suggested herein wherein first high risk individuals are identified and following their identification, only these identified individuals are administered a zinc derivative at a level approximating the minimum daily requirement for zinc.

I claim:

1. A method to prevent the occurrence of neonatal jaundice in a population of human infants which method comprises administering to a set of members of the population who exhibit above-normal carbon monoxide production, after having been subjected to a screening procedure to determine above-normal carbon monoxide production, an amount of zinc protoporphyrin or a derivative thereof effective to reduce the production of bilirubin to a level wherein production of carbon monoxide is normal.

2. The method of claim 1 wherein CO production has been measured as $ET_{CO}$.

3. The method of claim 1 wherein each infant has been tested for carbon monoxide production level at a time less than twelve hours after birth.

4. The method of claim 3 wherein the chemopreventive is administered to each infant immediately after the infant is shown to be a member of the set.

5. The method of claim 1 wherein said effective amount is approximately is 0.1-100 $\mu$mol of zinc ion/kg.

6. The method of claim 1 wherein the zinc protoporphyrin or derivative thereof has the formula

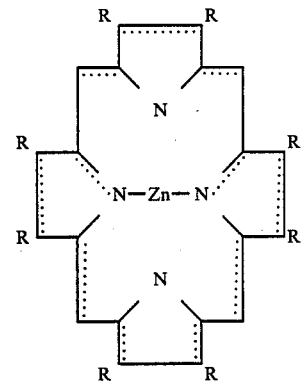

wherein
each R is independently selected from the group consisting of H and lower alkyl or alkenyl (1-6 C) optionally containing one or more functional groups; and
the dotted lines represent the presence or absence of a pi-bond at the indicated location.

7. The method of claim 1 wherein the zinc protoporphyrin or derivative thereof is selected from zinc protoporphyrin and zinc mesoporphyrin.

8. A method to control bilirubin production, as measured by carbon monoxide production in a human infant which method comprises administering to an infant overproducing carbon monoxide, an amount of zinc-protoporphyrin or a derivative thereof effective to reduce carbon monoxide production to normal levels.

9. The method of claim 8 wherein the effective amount is 0.1-100 umol/kg body weight.

10. The method of claim 8 wherein the zinc protoporphyrin or derivative thereof has the formula

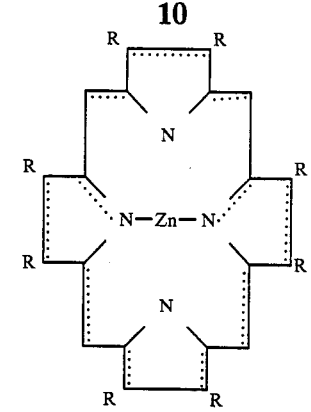

wherein
each R is independently selected from the group consisting of H and lower alkyl or alkenyl (1-6 C) optionally containing one or more functional groups; and
the dotted lines represent the presence or absence of a pi-bond at the indicated location.

11. The method of claim 8 wherein the zinc protoporphyrin or derivative thereof is selected from zinc protoporphyrin and zinc mesoporphyrin.

* * * * *